US005664368A

United States Patent [19]
Sándor

[11] Patent Number: 5,664,368
[45] Date of Patent: Sep. 9, 1997

[54] PROCESS FOR THE DEVELOPMENT OF NOVEL TYPE OF PLANTS WITH NITROGEN-FIXING CAPACITY ALSO IN THEIR LEAVES

[75] Inventor: Varga Szilárd Sándor, Budaörs, Hungary

[73] Assignee: Piacfejlesztesi Alapitvany, Hatvani, Hungary

[21] Appl. No.: 313,161

[22] PCT Filed: Apr. 9, 1993

[86] PCT No.: PCT/HU93/00020

§ 371 Date: Nov. 3, 1994

§ 102(e) Date: Nov. 3, 1994

[87] PCT Pub. No.: WO93/20685

PCT Pub. Date: Oct. 28, 1993

[30]     Foreign Application Priority Data

Apr. 10, 1992 [HU] Hungary ................................ 92 01218

[51] Int. Cl.[6] ................................ A01H 3/00; A01H 4/00
[52] U.S. Cl. ........................ 47/58; 47/DIG. 1; 800/200; 435/172.1; 435/430; 435/430.1; 71/7
[58] Field of Search ...................... 800/200, 250, 800/208; 47/58, DIG. 2; 425/172.1

[56]              References Cited

PUBLICATIONS

Carlson et al. "Forced association between higher plant and bacterial cells in vitro." Nature 252:393–395 Nov. 29, 1974.

Linsmaier et al. "Organic growth factor requirements of tobacco tissue cultures." Physiologia Plantarum 18: 112 1965.

*Primary Examiner*—Gary Benzion
*Attorney, Agent, or Firm*—Keil & Weinkauf

[57]              ABSTRACT

The invention relates to a process for developing plants of novel type being capable of nitrogen-fixation also in their leaves. The process of the invention comprises inoculating plant protoplasts, cells, tissues, embryos or organs grown and/or treated under in vitro conditions with bacteria belonging to the family of Azotobacteraceae, then cocultivating the thus-obtained culture at a temperature of 15° to 35° C. and, if desired, propagating and/or regenerating the whole plant under in vitro conditions on or in a culture medium containing nitrogen and main carbon source(s) utilizable only by the plant cells as well as optionally other additives. The process of the invention ensures a well-balanced growth of the plant together with the bacteria.

10 Claims, 2 Drawing Sheets

PROCESS FOR THE DEVELOPMENT OF NOVEL TYPE OF PLANTS WITH NITROGEN-FIXING CAPACITY ALSO IN THEIR LEAVES

This invention relates to a process for developing novel type of plants which are capable of fixing nitrogen also in their leaves.

It is known that nitrogen is the main limiting factor of agricultural plant cultivation since the supply of nitrogen by fertilization is albeit efficient but very expensive and is accompanied by an extreme environmental pollution. The worldwide spreading conception of cultivation, the conception of "maintainable development" gives preference to the production based on internal resources instead of using external ones. Accordingly, it is suitable to provide the nitrogen supply of plants by utilizing the possibilities implied in the biological nitrogen-fixation instead of employing fertilizers [Plant and Soil 141, 1–12 (1992)]. However, only some procaryotes (diazotrophs) are able to fix the atmospheric nitrogen gas.

The so-called aerobic nitrogen-fixing bacteria, the members of genera Azomonas, Azotobacter, Beijerinckia and Derxia belonging to the family of Azotobacteraceae [Bergey's Manual of Determinative Bacteriology, 8th ed., Williams and Wilkins, Baltimore, page 253 (1974)], which are capable of an efficient nitrogen-fixation even at atmospheric oxygen levels, are unable in the nature to be incorporated into the inner tissue spaces of plants [Azotobacteraceae: the Taxonomy and Ecology of the Aerobic Nitrogen-fixing Bacteria, Academic Press, New York (1979)] and to spread in the intercellular spaces although it could be proven that, when settling down on the roots or on the outer surfaces of leaves, these species are capable to provide the nitrogen demand of some plants to a significant or whole extent [J. Gen. Microbiol. 71, 103–116 (1972); J. Gen. Appl. Microbiol. 25, 261–271 (1979); Can. J. Bot. 69, 2296–2298 (1991)]. The so-called microaerophilic diazotrophs, fixing the nitrogen at low oxygen levels, are only able to form intercellular endosymbioses [Nitrogen-fixing Bacteria in Nonleguminous Crop Plants, Sci. Tech. Publishers/Springer-Verlag, Madison, Wis., pp. 84–88 (1987)] which, however, can fix nitrogen gas only in the roots, i.e. far from the site of photosynthesis.

Up to the present, two studies have been carried out to cocultivate Azotobacter species with plant cells under in vitro conditions.

In the first experiment [Nature 252, 393–395 (1974)] an adenine-auxotrophic *Azotobacter vinelandii* mutant strain was cocultivated with carrot cells on a sucrose-containing medium, which was nitrogen-free or contained nitrogen in an amount insufficient for plant growth. The thus-obtained mixed callus cultures kept growing for 18 months, showed nitrogen-fixing activity and the bacteria could be observed among the living plant cells. This method has, however, several drawbacks: an auxotrophic mutant strain of Azotobacter species is used which is difficult to isolate due to its high number of "chromosomes" [J. Bacteriol., 138, 871–877 (1979)]; the growth of the cultures is slow; the system is unstable in the presence of nitrogen; no plant could be regenerated; the applicability of the method is limited to a few intensely studied species because of the low number of auxotrophic strains.

In the other experiment [Z. Pflanzenphysiol. 95, 141–147 (1979)] the bacteria engulfed the plant tissue and destroyed it. Thus, it became impossible to cultivate for a long period and to develop a nitrogen-fixing plant.

The aim of the present invention is to eliminate the drawbacks of the processes known in the art and to develop a process, by the use of which it becomes simply possible to develop under in vitro conditions a plant capable of nitrogen-fixation by its leaves also and containing bacteria belonging to the Azotobacteraceae family in its inner spaces, too.

The invention is based on the recognition that under in vitro conditions it is possible to incorporate prototrophic, rapidly growing bacteria belonging to the family of Azotobacteraceae, which are capable of nitrogen-fixation even at atmospheric oxygen levels, to the inner plant spaces and to colonize them in the inner spaces when nutrient sources are added which provide less favourable nutriment supply instead of the optimum nutriment supply practically used for plant cells. Namely, it has been recognized that, by using such a nutriment supply, the plant and bacterial cells can grow evenly and well-balancedly whereas on traditional media used for cultivating plant materials in vitro, due to their growth rate being by an order higher, the bacteria overgrow the tissues of the host plant and destroy them.

Furthermore, the invention is based on the recognition that the well-balanced growth of both partners can be maintained during in vitro cultivation by using main carbon source(s) which can be metabolized only by the plant, i.e. which is (are) metabolized by the plant cells and only the products of the plant metabolism can be utilized for the bacterial growth to an extent required for simultaneous development. This recognition is surprising since in the cocultivation the growth of the cultures is provided by carbon source(s) which are utilized by the plant cells in only a lower degree and which are practically used only for metabolism examinations and only occasionally for plant cultures in vitro.

The invention is based on the further recognition that the providing of an optimum nitrogen source in the nutrient medium is also necessary for plant materials cocultivated with a nitrogen-fixing bacterium in order to develop a whole plant from the cultures with a high probability and number. This means that no in vitro symbiotic relationship is needed for the formation of an in vivo symbiotic relationship and thus the above aim can be achieved by a non-symbiotic cocultivation, too. This recognition is surprising since till now the opinion was predominant that in the case of such cocultivation the plant cultures should be cultured on nitrogen-free media or on media of low nitrogen-content, for making the growth of the plant tissues dependent upon the nitrogen fixation of the bacteria.

Finally, the invention is based on the recognition that members of the Azotobacter, Azomonas, Beijerinckia and Derxia genera can be preferably utilized to develop a novel type of nitrogen-fixing plants. This recognition is surprising since, according to our knowledge till now, these so-called free-living bacteria do not colonize in the inner spaces of plants under in vivo conditions and have no tendency to form such tight associations under natural conditions [Azotobacteraceae: The Taxonomy and Ecology of the Aerobic Nitrogen-fixing Bacteria; Academic Press, New York (1979)]. Thus, the widening of nitrogen-fixing symbioses to new plant species can be achieved not only by further-developing known natural symbioses and tight endophytic associations [Plant Soil 141, 13–39 (1992)].

Based on the above considerations the invention relates to a process for developing plants of novel type being capable of nitrogen-fixation also in their leaves. According to the invention plant protoplasts, cells, tissues, embryos or organs grown and/or treated under in vitro conditions are inoculated with bacteria belonging to the family of Azotobacteraceae, then the thus-obtained culture is cocultivated at a temperature of 15° to 35° C. and, if desired, propagated and/or the whole plant is regenerated at the same temperature under in vitro conditions on or in a culture medium containing nitrogen and main carbon source(s) utilizable only by the plant cells as well as optionally other additives.

The species of Azotobacter, Azomonas, Beijerinckia and Derxia genera belonging to the Azotobacteraceae family are preferably used as heterotrophic bacteria capable of nitrogen-fixation at atmospheric oxygen levels.

The vegetative cells, cysts and forms partially or totally deprived of the cell wall of bacteria are preferably used for inoculation.

Lactose, maltose, galactose, cellobiose, starch, raffinose and/or sorbitol are preferably employed as main carbon source(s) being utilizable only by the plant cells. These main carbon source(s) is (are) conveniently added in a concentration of at least 10 g/liter, preferably 20 to 40 g/liter, to the culture medium. In case of bacteria partially or totally deprived of their cell wall, the main carbon source(s) is (are) suitably used in a concentration of 0.35 to 0.75M.

In the process of the invention the pH values of the culture media are preferably adjusted to a value being optimum for the growth of the bacterium, this value being 5.5 to 9.5 for the genera Azotobacter, Azomonas and Derxia and 3 to 9.5 for the genus Beijerinckia.

In the process of the invention, the additional $Ca^{2+}$ demand required for the growth of some species of the Azotobacter and Azomonas genera is preferably provided by adding calcium carbonate and/Or calcium chloride to the culture media preferably in an amount of 0.1 to 0.5 g/liter and 0.05 to 0.2 g/liter, respectively.

In vitro techniques known in the art, commonly used for treating, culturing or micropropagating, respectively, protoplasts, cells, callus tissues, embryos or sprouts are preferably used for developing and propagating the new-type of nitrogen-fixing plants.

"Supplementary" carbon sources, preferably sucrose or glucose, as well as vitamins, amino acids and growth-promoting agents can also be used in the process as additives utilizable also by the bacteria.

Figure 1:
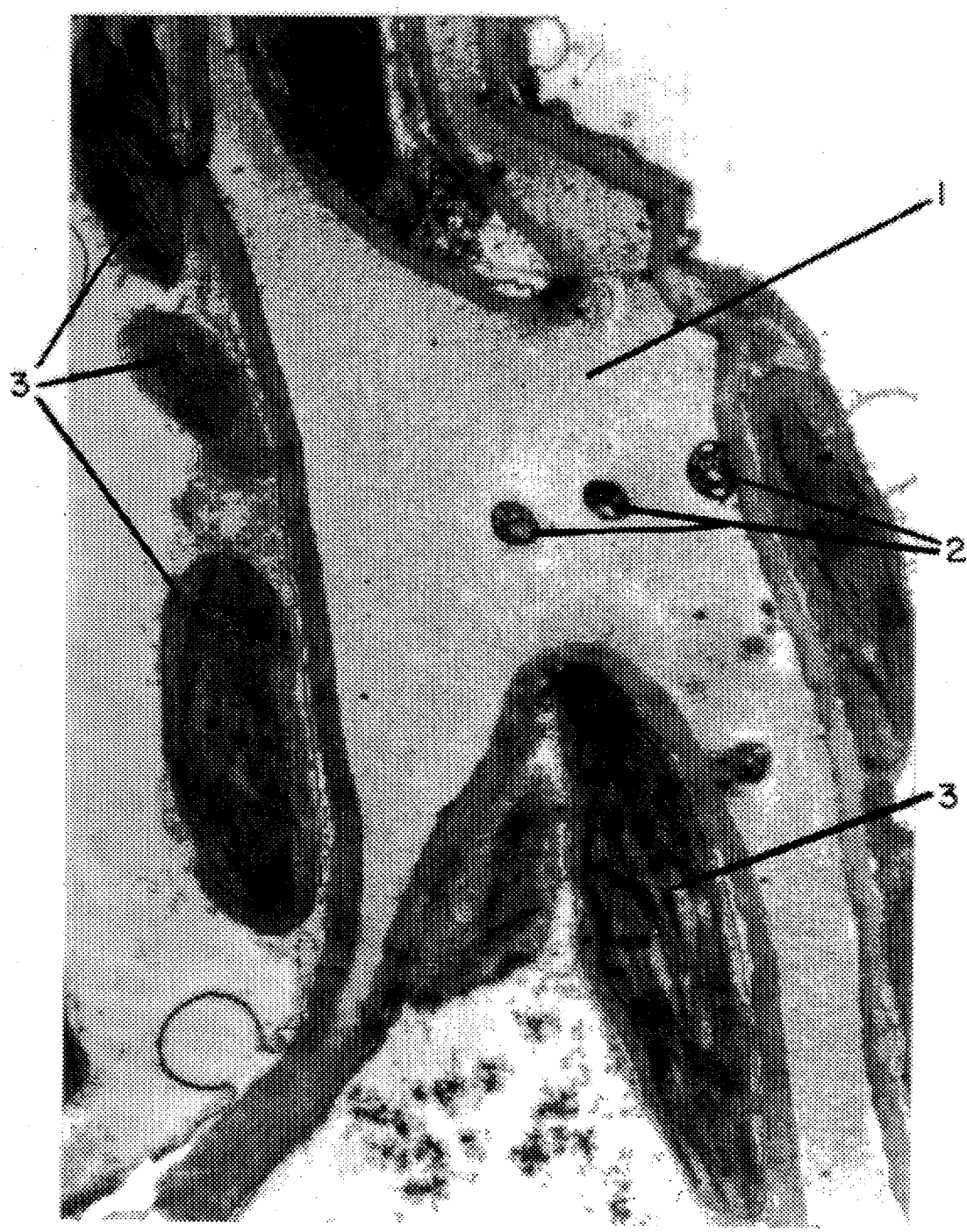
FIG. 1 is an electron-microscopic photograph of 16,000-fold magnification showing *Azomonas agtlis* cells incorporated to the intercellular spaces of leaf-stalk of carrot plant.

The main advantages of the process according to the invention can be summarized as follows.

a) The nitrogen-fixing plant prepared by the process of the invention is capable of nitrogen-fixation also in its leaves, so it demands no or only a little of any nitrogen-fertilization.

b) Both auxotrophic and prototrophic bacteria can be used.

c) Traditional in vitro techniques can be used.

d) The well-balanced growth of both the plant and bacteria is maintained.

e) The plant/bacteria endosymbioses can relatively rapidly develop.

f) Any plant species and any plant part can be used in the process.

g) The developed symbioses can rapidly be propagated by using in vitro methods, preferably micropropagation.

h) The efficiency of the novel nitrogen-fixing plant can be increased by using a bacterial mutant overproducing nitrogenase enzyme and/or releasing a large amount of fixed nitrogen.

The process according to the invention is further illustrated by the following non limiting Examples.

EXAMPLE 1

After washing out the sucrose rests, a carrot-cell suspension was inoculated with a cell suspension ($10^6$ to $10^8$ cells/ml; vegetative cells and cysts) of *Azotobacter vinelandii* (DSM 87), then the collected cells were cultivated at 17° to 22° C. on an agar-solidified callus-forming MS culture medium [pH=6.2; Physiol. Plant 15, 473–494 (1962)] containing 0.5 mg/liter of 2,4-dichlorophenoxyacetic acid (2,4-D) as plant hormone, and 30 g/liter of lactose as single carbon source. The thus-grown callus mass was transferred to a similar MS-medium containing no 2,4-D hormone and the cultivation was continued under identical conditions. The thus-regenerated plants were planted into soil and after 2 months the bacterial content of the leaves was determined after surface-sterilization (0.2% solution of $HgCl_2$ for 1.5 min.) and homogenization. The leaves contained $10^4$ to $10^5$ bacteria/g of fresh leaf weight.

The same experiment was repeated on the same MS-medium with the difference that the culture medium did not contain 2,4-D hormone, that is the plant cell suspension was inoculated with a cell suspension of *Azotobacter vinelandii* (DSM 87) and cultivated at 17° to 22° C. on the agar-solidified MS-culture medium containing no 2,4-D. The thus-regenerated plants were examined in the same way as in case of the plants regenerated from the callus mass grown on hormone-containing culture medium. The bacterial content of the leaves was practically the same, that is $10^4$ to $10^5$ bacteria/g of fresh leaf weight.

The nitrogen-fixation by the leaves was proven by examining the acetylene reduction in an atmosphere containing 10% by volume of acetylene without surface sterilization (755 nanomoles of $C_2H_4$/g of fresh leaf/24 hours) or after surface sterilization (530 nanomoles of $C_2H_4$/g of fresh leaf/24 hours) by incubating the leaves tested for 14 hours of light (1200 lux) and 10 hours of darkness at 25° C. The culture medium contained 0.1 g/liter of calcium carbonate as supplementary $Ca^{2+}$ source.

EXAMPLE 2

Carrot calluses were inoculated in the way as described in Example 1 by *Azomonas agilis* (DSM 375) cells, then the plants were cocultivated and regenerated at 27° to 32° C. on a culture medium (pH=7.3) containing 30 g/liter of lactose as main carbon source and 0.1 g/liter of sucrose as supplementary carbon source.

The bacteria regenerated and incorporated to the plant were counted after surface sterilization ($10^5$ to $10^6$ bacteria/g of fresh root and $10^6$ to $10^7$ bacteria/g of fresh leaf) and shown by electron microscope. In the electron-microscopic photograph of FIG. 1 one can see the microorganisms 2 incorporated into the intercellular space 1 surrounded by the living plant cells containing chloroplasts 3. After surface sterilization 1 g of leaf reduced 278 nanomoles of acetylene to ethylene in a day whereas 266 nanomoles of acetylene were reduced by 1 g of root in a day.

EXAMPLE 3

Figure 2:
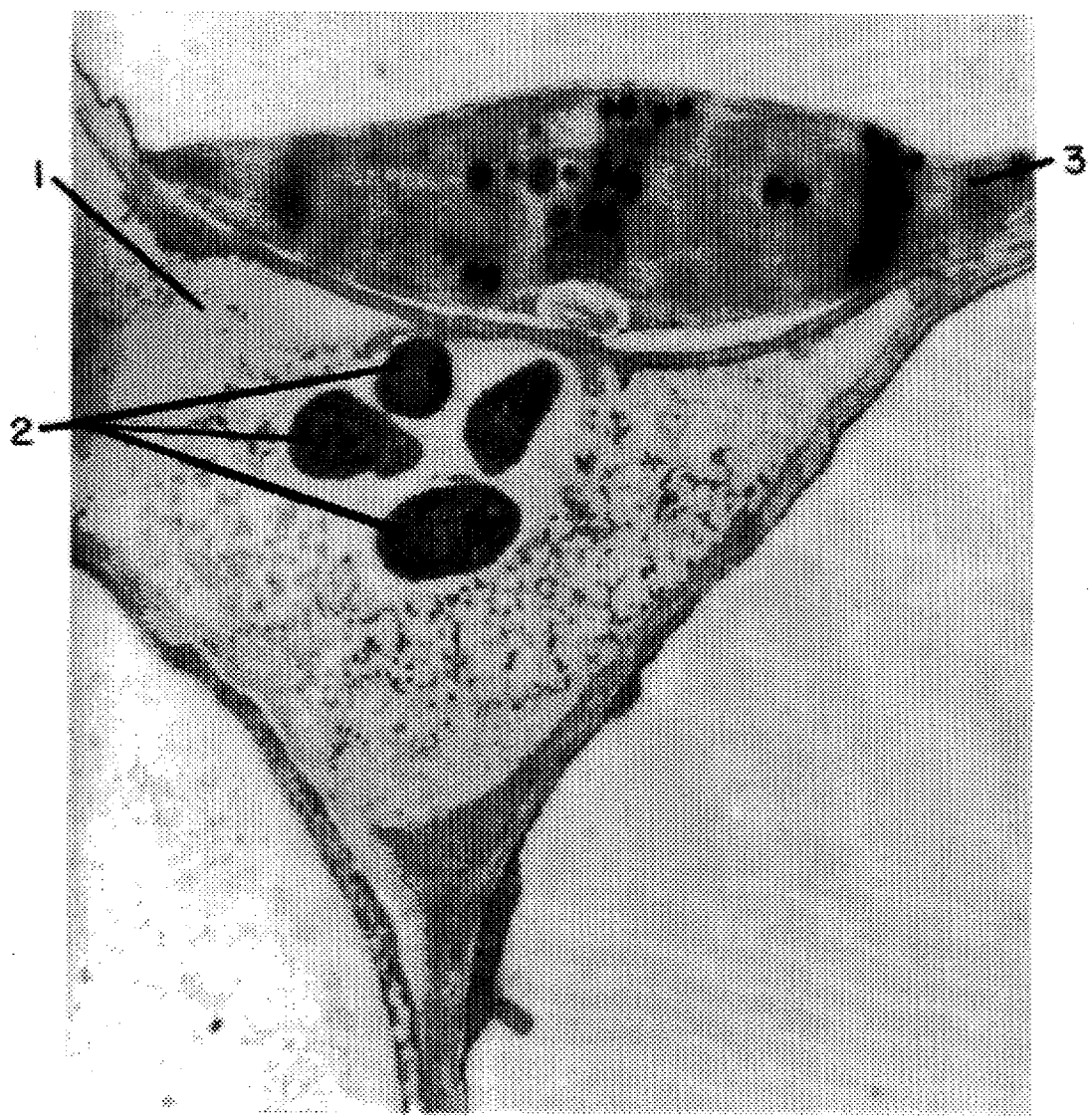
FIG. 2 is an electron-microscopic photograph of 18,000-fold magnification showing *Azomonas insignis* cells incorporated to the intercellular spaces of leaf-stalk of carrot plant.

A carrot cell suspension was inoculated with *Azomonas insignis* cells (ATCC-12523) in the same way as described in Example 1. The culture medium contained 30 g/liter of galactose as main carbon source and 2.5 g/liter of glucose as supplementary carbon source (pH=8.3, 27° to 33° C., 0.1 g of calcium chloride). The bacterial content of the regenerated plant was detected by electron microscope ($10^5$ bacteria/g of fresh leaf/day). An electron-microscopic photograph is shown in FIG. 2 with microorganisms 2 incorporated into the intercellular space 1 and with chloroplast 3 of the plant cells.

EXAMPLE 4

The shoot culture of tobacco was inoculated through a cut surface with a cell-wall-free (L-form) culture of *Azotobacter paspali* (ATCC 23833) (induced on a culture medium containing 100 ppm of penicillin G, stabilized with 0.5M of glucose). The cultures thus obtained were cultivated on a culture medium containing 0.5M of maltose, 100 ppm of penicillin-G and 0.25 g of calcium carbonate (pH=7.3) for 2 months. Subsequently, the cultures were cultivated while omitting the penicillin-G and then decreasing the maltose content of the culture medium to 10 g/liter. After planting out, the nitrogen-fixing activity of the leaves was found after surface sterilization to be 800 nanomoles of $C_2H_4$/g of fresh leaf/24 hours.

EXAMPLE 5

A carrot-cell suspension was inoculated with a suspension of *Beijerinckia mobilis* (DSM 2326) in the way as described in Example 1 and the cultures were cocultivated on a culture medium containing 40 g/liter of lactose (pH=5.4, without $Ca^{2+}$ supplement). The nitrogen-fixing activity of the leaves of the regenerated plant was determined by the acetylene-reduction test and was found to be 180 nanomoles of $C_2H_4$/g of fresh leaf/24 hours.

EXAMPLE 6

After inoculating carrot cells with a *Derxia gumnosa* (ATCC 15994) suspension in the way as described in Example 3 (pH=7.2), the nitrogen-fixing activity of the leaves of the regenerated plant could be demonstrated by the acetylene-reduction test.

What we claim is:

1. A process for developing plants which are able to fix nitrogen in their leaves, which comprises inoculating plant protoplasts, cells, tissues, embryos or organs grown and/or treated under in vitro conditions with bacteria belonging to the family of Azotobacteraceae, then cocultivating the thus-obtained culture at a temperature of 15° to 35° C. and, propagating and/or regenerating the whole plant under in vitro conditions in a culture medium comprising nitrogen and main carbon source(s) utilizable only by the plant cells.

2. A process as claimed in claim 1, which comprises using the species of the genera Azotobacter, Azomonas, Beijerinckia and Derxia belonging to the family of Azotobacteraceae.

3. A process as claimed in claim 2, which comprises using for inoculation the vegetative cells, cysts, or forms of bacteria partially or totally deprived of their cell wall.

4. A process as claimed in claim 1, which comprises using lactose, maltose, galactose, cellobiose, starch, raffinose and/or sorbitol as main carbon source(s) being utilizable only by the plant cells.

5. A process as claimed in claim 1, which comprises adding the main carbon source(s) in a concentration of at least 10 g/liter, preferably 20 to 40 g/liter, to the culture medium.

6. A process as claimed in claim 1, which comprises adding the main carbon source(s) in a concentration of 0.35 to 0.75M to the culture medium for bacteria partially or totally deprived of their cell wall.

7. A process as claimed in claim 1, which comprises maintaining the pH value of the culture medium between 5.5 and 9.5 for bacteria belonging to the genera Azotobacter, Azomonas or Derxia and between 3 and 9.5, respectively, for bacteria belonging to the genus Beijerinckia.

8. A process as claimed in claim 1, which comprises using 0 to 0.5 g/liter of calcium carbonate and/or 0 to 0.2 g/liter of calcium chloride as other additives when Azotobacter and Azomonas genera are employed.

9. A process as claimed in claim 1, wherein the culture medium further comprises a supplementary carbon source, vitamins, amino acids and growth-promoting agents.

10. A process as claimed in claim 9, wherein the supplementary carbon source is sucrose or glucose.

* * * * *

UNITED STATES PATENT AND TRADEMARK OFFICE
CERTIFICATE OF CORRECTION

PATENT NO.: 5,664,368

DATED: September 9, 1997

INVENTOR(S): VARGA, Szilard Sandor

It is certified that error appears in the above-identified patent and that said Letters Patent is hereby corrected as shown below:

On the cover page, under "United States Patent [19]", delete "Sándor"
and replace with --VARGA--.

On the cover page, item [75], "Varga Szilárd Sándor" should be --Szilárd Sándor Varga--

Signed and Sealed this

Sixteenth Day of December, 1997

*Attest:*

BRUCE LEHMAN

*Attesting Officer*  *Commissioner of Patents and Trademarks*